US009272292B1

(12) United States Patent
Munson et al.

(10) Patent No.: US 9,272,292 B1
(45) Date of Patent: Mar. 1, 2016

(54) ELECTRONIC BIOLOGICAL ELIMINATOR FOR INHIBITING BIO-FILM AND MICROORGANISM DEVELOPMENT IN FUELS AND LUBRICANTS

(75) Inventors: Gerald L. Munson, Madison, CT (US); Daniel P. McCormick, Turner, ME (US)

(73) Assignee: MCCORMICK AND MUNSON TECHNOLOGIES, LLC, Madison, CT (US)

( * ) Notice: Subject to any disclaimer, the term of this patent is extended or adjusted under 35 U.S.C. 154(b) by 988 days.

(21) Appl. No.: 13/295,706

(22) Filed: Nov. 14, 2011

Related U.S. Application Data

(60) Provisional application No. 61/413,095, filed on Nov. 12, 2010.

(51) Int. Cl.
*C02F 1/48* (2006.01)
*A61L 2/00* (2006.01)
*B03C 5/00* (2006.01)

(52) U.S. Cl.
CPC .. *B03C 5/00* (2013.01); *B03C 5/005* (2013.01)

(58) Field of Classification Search
CPC .................................. B03C 5/00; B03C 5/005
USPC ........................... 210/748.01–748.04; 422/22
See application file for complete search history.

(56) References Cited

U.S. PATENT DOCUMENTS 3,246,144 A 4/1966 Beall et al.
4,007,007 A 2/1977 Gazda
4,886,593 A 12/1989 Gibbs
4,954,263 A * 9/1990 Woodhouse .................. 210/695
5,626,768 A 5/1997 Ressler et al.
5,655,210 A * 8/1997 Gregoire et al. .............. 422/186
6,497,839 B1 12/2002 Hasegawa et al.
7,176,018 B2 2/2007 Tai et al.
8,740,600 B1 * 6/2014 Gomes .................. 425/174.8 E
2008/0319372 A1 12/2008 Palti et al.

FOREIGN PATENT DOCUMENTS

GB 2452916 A 3/2009

OTHER PUBLICATIONS

Standard Test Method for Adenosine Triphosphate (ATP) Content of Microorganisms in Fuel, Fuel/Water Mixtures and Fuel Associated Water, Copyright Astm International, Nov. 2, 2011; Designation: D7463-08; pp. 1-7.

(Continued)

*Primary Examiner* — Kevin Joyner
(74) *Attorney, Agent, or Firm* — DeLio, Peterson & Curcio LLC; Kelly M. Nowak

(57) ABSTRACT

Apparatus, systems and methods for subjecting biological contaminated liquid fuels and/or liquids to an oscillating electric field for an extended duration within a treatment vessel that has a defined cavity having an insulating fill material encasing a number of insulating flow tubes each having at least one conductive body therein. The defined cavity also has one or more reservoirs in communication with the insulating flow tubes. An oscillating electric field is generated within the insulating flow tubes and reservoirs, whereby a biologically contaminated liquid fuel and/or lubricant is subjected to this oscillating electric field for an extended time to inhibit proliferation of these biological contaminants within the liquid fuels and/or lubricants.

18 Claims, 6 Drawing Sheets

(56) References Cited

OTHER PUBLICATIONS

Microbial Contamination Control in Fuels and Fuel Systems Since 1980—A Review, Frederick J. Passman, Ph.D., Fellow STLE; Biodeterioration Control Associates, Inc., Princeton, NJ 08543, USA; pp. 1-45.

An Effect of Magnetic Field Exposure on Microorganisms Associated With Fuel Oil, Michael Kugele & Andrew B.Yule, School of Ocean Sciences, University of Wales, Bangor, UK; Maher Kalaji, Department of Chemistry, University of Wales, Bangor, UK.; Bifouling, 1999, vol. 14(3), pp. 197-211.

A Micro Cell Lysis Device, S.W. Lee, H. Yowanto and Y.C. Tai, Caltech Micromachining laboratory, Electrical Engineering, California Institute of Technology, Clinical Micro Sensors, Inc., Pasadena, CA; pp. 443-447. 1998.

* cited by examiner

| Bio-Film on Slide in Fuel Phase Count pg ATP / $CM^2$ | | | | |
|---|---|---|---|---|
| Time (days) | Control | BCA | BCA + UV | EBE |
| | | | | |
| 0 | 0 | 0 | 0 | 0 |
| 15 | 73 | 480 | 50 | 120 |
| 30 | 20,000 | 27 | 4,700 | 62 |
| 45 | 24,500 | 34 | 1,300 | 15 |
| | | | | |
| Survivors as % of Control | 100 % | 0.138 % | 5.306 % | 0.0612 % |
| Kill Ratio | 0 | 99.862 % | 94.694 % | 99.94 % |

BioFilm Growth in Fuel After Non Chemical EBE Treatment
(Pg ATP / cm^2 vs. Days After Treatment in Microcosim)

| Bio-Film on Slide in Water Phase Count pg ATP/CM$^2$ | | | | |
|---|---|---|---|---|
| Time (days) | Control | BCA | BCA + UV | EBE |
| | | | | |
| 0 | 0 | 0 | 0 | 0 |
| 15 | 265 | 810 | 180 | 190 |
| 30 | 129000 | 33 | 720 | 15 |
| 45 | 25000 | 12 | 15 | 20 |
| | | | | |
| Survivors as % of Control | 100 % | 0.048 % | 0.06 % | 0.08 % |
| Kill Ratio | 0 | 99.95 % | 99.94 % | 99.92 % |

BioFilm Growth in Water After Non Chemical EBE Treatment
(Pg ATP / cm^2 vs. Days After Treatment in Microcosim)

ELECTRONIC BIOLOGICAL ELIMINATOR FOR INHIBITING BIO-FILM AND MICROORGANISM DEVELOPMENT IN FUELS AND LUBRICANTS

BACKGROUND OF THE INVENTION

1. Field of the Invention

The present invention relates to electronically eliminating or inhibiting the presence and reproduction of biological contaminants within fluid fuels or lubricants, tanks, or piping systems.

2. Description of Related Art

It has been known since the late 1800's that biological contaminants exist in hydrocarbon fuels. For instance, fungi and microbes (e.g., bacterium) were found to have been living and reproducing on purely hydrocarbon diets. Various other types of biological contaminants have also been reported in petroleum products, fuels and fuel systems over the years.

Biological contaminants are undesirable within flowing fluids, especially liquid fuels and lubricants, due to their tendency to grow and aggregate into clumps that form slime or a film, often referred to as a biofilm or a biomass. Both biological slime and biofilms generally grow at the bottoms of storage and piping systems, and include multiple species of contaminants that cooperate together in destructive ways by casting off filaments and/or tendrils that coat the sensors and filters within the filter tanks. Larger pieces of debris from these agglomerated biological contaminants can break off over time to abruptly decrease or even stop system performance.

It has also been shown that microbes within the biological contaminants can lead to microbial induced corrosion at the containment wall. This type of corrosion is created as an electrical phenomenon in combination with several processing conditions that cause microbes to separate metal components from the liquid. These separated metal components accumulate as acid byproducts including, for example, hydrochloric, nitric, nitrous or sulfuric acids, all of which deteriorate the fluid system.

Several approaches have been developed in order to avoid liquid fuel or lubricant system corrosion and deterioration. These approaches include chemical treatments as well as physical treatments and/or approaches. Chemical techniques for killing microbes involve the use of specially manufactured chemical micro-biocides that poison the biological cells known to affect and deteriorate fuels and lubricants. Many of these micro-biocides are controlled and government regulated due to their toxicity and difficulty of disposal. Often, when chemical biocides are used to eliminate microbes in liquids, the waste generated by the filtered liquid is toxic and must be carefully removed and disposed of so as not to contaminate the environment. For instance, ethylene glycol monomethyl ether (EGME), was commonly used as both a micro-biocide and a deicing agent for aircraft, however, its use has ceased due to its environmental toxicity. As such, many chemical treatments are slowly falling out of use due to their toxicity.

Physical treatments for killing microbes in liquids are typically broken into two primary categories, cell removal and cell disruption. Filtration is the most common cell or microbe removal technology. Other known cell disruption technologies include electrochemical, ultrasound, microwave, germicidal ultraviolet light (UV) and magnetic fields.

Electrochemical approaches are used in aqueous (i.e., water-based) liquid flows where current is conducted directly through the water to form short-lived chemistries in the zone of conduction that kill the bacteria. However, in highly non-conductive fuels and lubricants, electrochemical approaches are inefficient and often not viable. Ultrasonic techniques have also been implemented to disinfect aqueous media (e.g., drinking water). Yet, these techniques often require 60 minutes, or more, to achieve a kill rate of over 90%.

Microwave techniques enable the absorption of the microwaves into the aqueous molecular structures, and as such, are often used for sterilization of liquid food products. The relatively low energies used in microwave techniques may oxidize any alkynes present in fuels or lubricants. As such, the tendency for alkynes to oxidize at relatively low energies and damage the fuel by oxidation results in these approaches to be economically undesirable for fuels and/or lubricants.

Germicidal UV implement short wavelength ultraviolet radiation to destroy bacteria, molds and other bacterial organism for water treatment, typically in heating, ventilation and air-conditioning applications. In doing so, UV lamps at 185 nm and 254 nm light produce ozone with the 185 nm wavelengths and hydroxide radicals on instruction of the ozone with the 254 nm wavelength. However, these low powered ultraviolet sources are not sufficient for destroying bacteria, molds and other bacterial organisms in fuels and lubricants. Because most of the UV Energy was adsorbed by the first 10 um of fuel.

Magnetic field techniques use strong permanent magnets to damage cells as they pass by these fields at moderate flow rates. The magnetic fields cause any contaminants within the liquid to move back and forth until this movement causes the contaminant to break apart or split. The magnetic fields are passive fields that only break or split the contaminants into pieces, and do not further treat such contaminants thereafter. The split and/or broken pieces of contaminants continue to maintain their genetic make-up intact and unchanged, such that, these fragments or pieces are capable of growing, reproducing and even taking on genetic material or code from other contaminants. As such, any contaminant or fragment thereof having been passed through a magnetic field remains to be capable of growing into a biofilm or biomass. Magnets depend on fluids passing extremely close to concentrated field lines, at high velocity to create a large enough coupling, to influence the microbe. Most magnetic systems utilize open channels to limit the differential pressure across the device, rendering them less effective.

Therefore, a need continues to exist for improved non-chemical micro-inhibitors for systems, apparatus and methods that eliminate and destroy biological contaminants and microbes within liquid fuels and/or lubricants, and render any remaining biological contaminants within the treated effluent unviable.

SUMMARY OF THE INVENTION

Bearing in mind the problems and deficiencies of the prior art, it is therefore an object of the present invention to provide electronic systems, apparatus and methods that eliminate and destroy biological contaminants from liquid fuels and/or lubricants.

It is another object of the present invention to provide electronic systems, apparatus and methods that alter the genetic make-up of biological contaminants and microbes within liquid fuels and/or lubricants to render such contaminants unviable within the treated fuel effluent.

A further object of the invention is to provide electronic systems, apparatus and methods that easily, efficiently and quickly render inactive, biological contaminants and microbes within liquid flowing fuels and/or lubricants.

Another object of the present invention is to provide electronic systems, apparatus and methods that prevent biological contaminants and microbes within liquid flowing fuels and/or lubricants to propagate thereby resulting in minimal filtered waste for removal and disposal.

Still other objects and advantages of the invention will in part be obvious and will in part be apparent from the specification.

The above and other objects, which will be apparent to those skilled in the art, are achieved in the present invention which is directed to in a first aspect a treatment apparatus for inhibiting biological contaminant proliferation within fuels and lubricants. The treatment apparatus includes exterior walls defining a cavity of the treatment apparatus; an insulating fill material within a portion of the cavity; an even number of a plurality of insulating flow tubes encased within the insulating fill material, the insulating fill material isolating the flow tubes from one another; at least one reservoir residing in fluid communication with the plurality of insulating flow tubes within the cavity; and at least one conductive body within each of the plurality of insulating flow tubes, adjacent ones of the plurality of insulating flow tubes having alternating oppositely charged conductive phases of energy to generate an oscillating electric field within the plurality of insulating flow tubes and within the at least one reservoir to treat biological contaminants within fluid fuels and/or lubricants flowing through the treatment apparatus.

In another aspect the invention is directed to treatment system for inhibiting biological contaminant proliferation within fuels and lubricants. The treatment system includes a treatment apparatus with a defined cavity having an insulating fill material encasing a number of insulating flow tubes each having at least one conductive body therein, the defined cavity also having at least one reservoir in communication with the insulating flow tubes; a radio frequency oscillating electric field within the insulating flow tubes and within the at least one reservoir, the radio frequency oscillating electric field generated by the conductive bodies within the insulating flow tubes; and a biological contaminated fluid flowing through the treatment apparatus and contacting the radio frequency oscillating electric field within the insulating flow tubes and within the at least one reservoir, the radio frequency oscillating electric field affecting the biological contaminants within the fluid to inhibit the proliferation thereof within said fluid.

In yet another aspect, the invention is directed to a method for inhibiting biological contaminant proliferation within fuels and lubricants. The method includes providing a treatment apparatus with a defined cavity having an insulating fill material encasing a number of insulating flow tubes each having at least one conductive body therein, the defined cavity also having at least one reservoir in communication with the insulating flow tubes; energizing the conductive bodies within the insulating flow tubes to generate an oscillating electric field within the insulating flow tubes and within the at least one reservoir; flowing a liquid fuel and/or lubricant containing biological contaminants into the treatment apparatus; subjecting the liquid fuel and/or lubricant to the oscillating electric field within the at least one reservoir for a first treatment time; continuing to subject the liquid fuel and/or lubricant to the oscillating electric field within the insulating flow tubes for a second treatment time; and inhibiting proliferation of the biological contaminants within the liquid fuel and/or lubricant by said treatment of the liquid fuel and/or lubricant to the oscillating electric field for said first and second treatment times.

BRIEF DESCRIPTION OF THE DRAWINGS

The features of the invention believed to be novel and the elements characteristic of the invention are set forth with particularity in the appended claims. The figures are for illustration purposes only and are not drawn to scale. The invention itself, however, both as to organization and method of operation, may best be understood by reference to the detailed description which follows taken in conjunction with the accompanying drawings in which:

DESCRIPTION OF THE PREFERRED EMBODIMENT(S)

Figure 1:
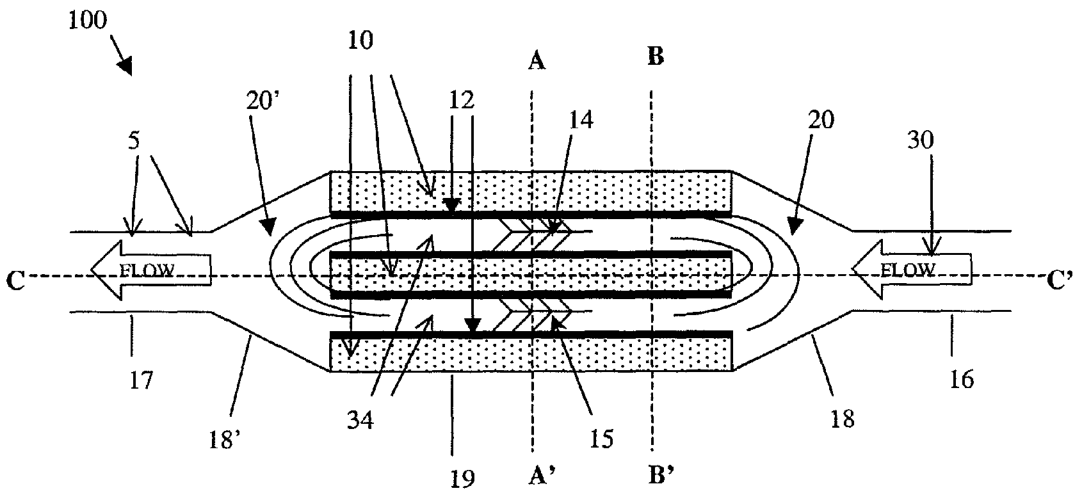
FIG. 1 is a cross sectional side view of a treatment vessel assembly in accordance with one or more embodiments of the invention along line C-C' as shown in FIGS. 2A-2B.

In describing the preferred embodiment of the present invention, reference will be made herein to FIGS. 1-12 of the drawings in which like numerals refer to like features of the invention.

Biological contamination is a major problem for fuels and lubricants in transit, storage and operating machinery. A variety of biological contaminants grow within the fuel and lubricant storage and transit systems by being drawn in with replacement air as the systems are emptied. With a few exceptions, the majority of liquid fuels and lubricants are hydrophilic adsorbing water from the atmosphere and providing a petroleum-water interface within the storage tank. This petroleum-water interface enables biological contaminants to grow and form slimes and biofilms.

A biofilm (also referred to as a biomass) is an aggregate of microorganism cells that adhere to each other and/or to a surface. In the development of a biofilm/biomass within liquid fuels and/or lubricants these microbes first aggregate on a surface within the environment in which such liquid resides, typically at an oil-water interface surface. This diffusion of the microbes and aggregation at such oil-water interface surface is often stopped at the fuel-water interface residing at the containment/pipe wall. Contaminant cell growth must be sufficiently robust to create large numbers of microbes contiguous to one another with continuing access to the nurturing environment. Again, the fuel-water tank-side interface is ideal for this process, or a low point in any piping system.

As the contaminant cells grow and reproduce, intracellular polymeric substances or slime develop, which binds the aggregate together and increases overall stability of the mass. The biofilms and/or slimes may become resuspended within the liquid, without warning, to abruptly block flowing fuel, filtration and/or lubricating systems. Filter blocking is the most noticed effect of bio-film development, and occurs without warning and may persist for long periods of time.

Also, as the contaminant cell mass continues to grow, the polar nature of such biomass generates a variety of acids that promote electrical currents as part of their life cycle to create Microbial Induced Corrosion (MIC) within the systems, which may promote faster growth of the biomass. This corrosion is difficult to detect, and often causes catastrophic breaching of storage, transport and filtration systems. Breakdown of the liquid fuel and lubricant storage, transport and filtration systems due to biological contaminant induced corrosion also unfortunately occurs without warning, which may lead to spillage or leak clean-up and remediation.

As discussed above, a number of conventional approaches to address biological contamination involve chemical attack of such biological contaminants. These chemical approaches involve adding or introducing a chemical composition or constituent into the fuels and lubricants to attack, breakdown and/or destroy the biological contaminants residing therein. Often, chemical approaches to bio-remediation are used to temporarily eliminate the bio burden on a batch basis. For instance, sulfur was typically added as a biocide to remove ant microbial agents from liquid fuels and lubricants However, it has been found that the chemicals used in fuel and lubricant bio-remediation, as well as the resultant waste generated from such chemical approaches, are all poisonous and/or carcinogenic requiring specialized care and extensive training to handle, remove and dispose of these materials safely. For instance, the use of sulfur has been discouraged due to its toxicity and difficulty of waste disposal. Further, all of these chemicals, and their resultant chemical waste, are returned to the environment when the fuel or lubricant is burned off. This return of poisons and carcinogens to the environment is undesirable, and in many instances, no longer accepted.

The present invention is directed to methods, apparatus and systems that cleanly, easily and efficiently destroy biological contaminants and microbes within liquid flowing fuels and/or lubricants, and output minimal biological waste. The various embodiments of the invention provide non-chemical approaches, as compared to the conventional chemical approaches, that eliminate and destroy biological contaminants from liquid fuels and/or lubricants, and render substantially any remaining biological contaminants within the treated fuel effluent inactive and/or unviable. The Electronic Biological Eliminator (EBE) of the invention utilizes radio frequency electrical energy to disrupt the metabolic functions of microbes and bacteria. As such, microorganisms within the liquid fuels and lubricants are unable to reproduce, thereby inhibiting and/or drastically reducing the growth of biofilms and microorganisms within these liquids.

The various embodiments of the invention are all directed to non-chemical approaches (i.e., no chemical compositions and/or constituents are added into the fuels and lubricants) of attacking, breaking down and/or destroying biological contaminants within fuels and lubricants that are treated in accordance with the invention. In doing so, the invention treats bacterium and microorganisms within liquid fuels and lubricants to an oscillating electric field that is generating within and throughout a majority of the liquid flow path. This radio frequency oscillating electric field alters the cell genetics of the microorganisms. Due to the extended electric field exposure times and the forces generated thereby that are applied to the microorganisms, the microorganisms are altered in a way that not only destroys or kills a majority of such microorganisms within the liquid flow, but also renders any undestroyed microorganisms detrimentally affected and unviable over time. As such, the invention provides minimal waste for removal and disposal.

Referring to the drawings, FIG. 1 shows an apparatus and system for an Electronic Biological Eliminator (EBE) of the invention for inhibiting biofilm and microorganism development in fuels and lubricants. The present apparatus and systems include a treatment vessel assembly 100 for altering biological contaminants in fuels and/or lubricants. The treatment vessel assembly 100 has exterior walls 5 for fluid containment composed of an insulating material. While the present invention is described in relation to the fluid being in a liquid state, it should be appreciated and understood that the invention may also be suitable for use with other known fluid states (e.g., a gas or gaseous state). This insulating material may include, for instance, a plastic material, PVC, fiberglass, nylon glass filled, or any other material that is chemically compatible with the fuels and/or lubricants treated therein. The exterior walls 5 of the assembly also have a thickness sufficient to withstand the internal pressures of the liquid being treated therein.

The treatment vessel assembly 100 includes an inlet port 16 for allowing a liquid to enter the assembly, flow through the assembly, and exit an outlet port 17. The treatment vessel allows liquid fuels and/or lubricants to flow in a single direction along a flow path 30 that travels from the inlet port 16 toward the outlet port 17. As will be appreciated and understood, the flow rate will vary depending upon the compositions of the liquid being treated, the viscosity of the liquid, the temperature within and external to the treatment vessel system, the internal width diameter of the components of the treatment vessel assembly, and the like. The treatment vessel assembly 100 also has a middle portion 19 residing between two reservoirs 18, 18' that hole the liquid during flow. The first reservoir 18 resides between the inlet port 16 and the middle portion 19 of the assembly, while the second reservoir 18' resides between the middle portion 19 and the outlet port 17.

In one or more embodiments the reservoirs 18, 18' are larger in diameter than the inlet 16 and outlet 17 ports, and have a depth extending into the assembly (i.e., distance between the end of the inlet port 16 and beginning of the middle portion 19) that is sufficient for treating the fuel and/or lubricant of interest. Again, it should be appreciated and understood that depending upon the fuel and/or lubricant being treated, the sizes and dimensions of the treatment vessel assembly 100 will vary so that it is suitable for efficiently and effectively treating such liquids.

As shown in FIG. 1, in one or more embodiments the first reservoir 18 may have a diameter at its liquid-entry side that is the same size as a diameter of at least the end of inlet port 16. Inlet port 16 may be substantially conical or tubular in shape. The diameter of the first reservoir 18 may gradually expand as it approaches the middle portion 19 of the assembly, at which point, the middle portion 19 and the liquid-exit end of the reservoir 18 have the same diameter. In the cross sectional view of FIG. 1, the reservoir 18 is shown as a trapezoidal shape, however, it should be appreciated that in a three-dimensional rendering of such drawing, the reservoir 18 may be in the shape of a trapezoidal prism or conical Liquid enters the narrower end of this trapezoidal prism from the adjacent inlet port 16, and is retained and circulated within this reservoir for a predetermined resonance treatment time, which is discussed further below, before it enters into the middle portion 19 of the assembly 100.

The middle portion 19 of the treatment vessel assembly 100 includes a plurality of insulated flow tubes 12 encased within an insulating fill material 10. In one or more embodiments, the two or more insulated flow tubes 12 may be encased within the insulating fill material 10. In other embodiments, 4 or more flow tubes (see, FIGS. 2A-B), 6 or more flow tubes (see, FIGS. 3A-B), or even more, may be encased within the insulating fill material 10 so long as the flow tubes 12 are present in an even number to accommodate two different high voltage phases applied to the assembly.

The assembly 100 includes an insulating fill material 10 residing substantially at the center of the treatment vessel assembly 100. This insulating fill material 10 securely holds and retains the flow tubes 12 therein, as well as insulates such flow tubes 12 from one another. In one or more embodiments, the insulating fill material 10 has a low conductivity, and a thermal coefficient of expansion (TCE) closely matched to the TCE's of both the flow tubes 12 and the outer wall material 5 of the assembly 100 itself. The insulating fill material 10 also preferably has a low thermal impedance to prevent assembly over-heating, a low dielectric constant to prevent influencing a wave shape of an oscillating electric field generated by the various embodiments of the invention, and prevents ingress of moisture into the assembly. The fill material 10 may be chosen so that it provides full insulation between connection points of external wiring 80 from outside the assembly, into and through the outer wall 5 and fill 10, and that make contact with conductive bodies residing inside the flow tubes 12.

For instance, the insulating fill material 10 may include, but is not limited to, an epoxy (e.g., a low dissipation factor poured epoxy), silicon, a plastic, a dielectric material, and the like. It should be appreciated and understood that this list of materials is not meant to limit the invention, and that depending upon the fuels and/or lubricants being treated, the material of the tubes 12 and the exterior 5 of the assembly, as well as all thermal, chemical and/or physical characteristics and properties to be taken into account, the insulating fill material 10 suitable for use in accordance with the invention may vary widely.

The treatment vessel assembly 100 also includes the plurality of flow tubes 12 embedded and secured within the insulating fill material 10 thereof. In one or more embodiment, these flow tubes 12 may be composed of an insulating material that has a low dissipation factor to prevent overheating, a low dielectric constant to prevent influencing the electric field wave-form, a high resistance to water, and not be affected by water. The material of the flow tubes 12 is also chosen so that these tubes 12 are compatible with the compositions of the fuel and/or lubricant to be treated through such tubes 12, and compatible with any required processing conditions (e.g., temperatures, pressures, flow rates, etc.) as may be necessary to treat the desired fuel and/or lubricant of interest. For instance, the flow tubes 12 may include, for instance, a plastic material, PVC, glass, fiberglass, nylon, Teflon®, and the like.

Within each flow tube 12 of the assembly 100 further includes at least one conductive emitter component. These conductive emitter components within the one or more flow tubes 12 generate an oscillating high voltage that is emitted to and trough the flow traveling into the flow tubes, through the flow tubes and out the flow tubes. Conductive emitters suitable for use in the invention may include those having low resistivity, and are non-corrosive in the presence of water.

Figure 2A:
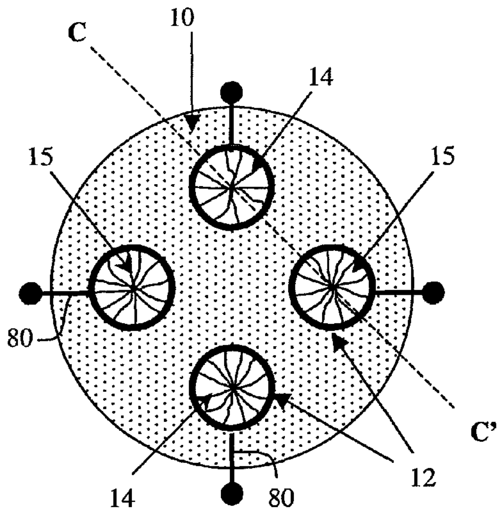
FIG. 2A is a cross sectional view along line A-A' of FIG. 1 showing the assembly having at least four flow tubes each having a conductive body for emitting energy.
Figure 2B:
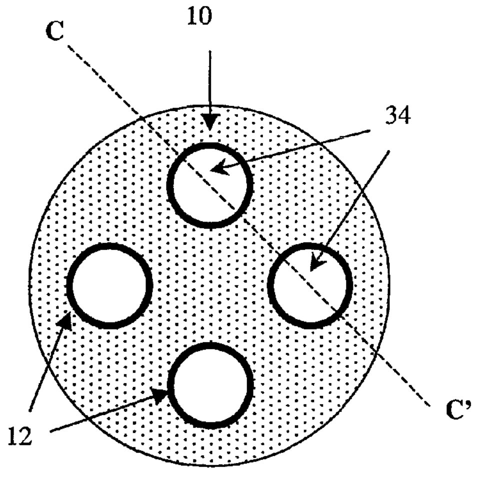
FIG. 2B is a cross sectional view along line B-B' of FIG. 1 showing an unimpeded portion of the flow tubes of FIG. 2A.
Figure 3A:
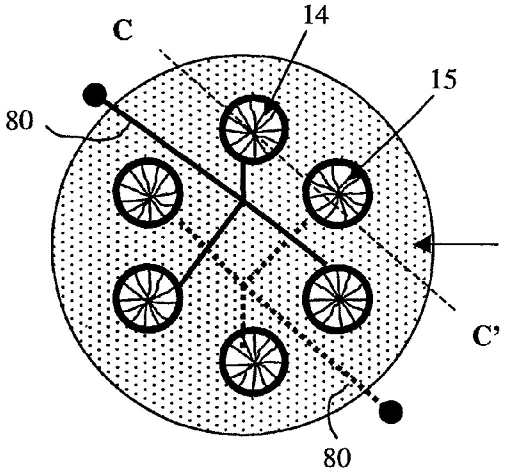
FIG. 3A is a cross sectional view along line A-A' showing a treatment vessel assembly in accordance with one or more embodiments having at least six flow tubes each having a conductive body for emitting energy.
Figure 3B:
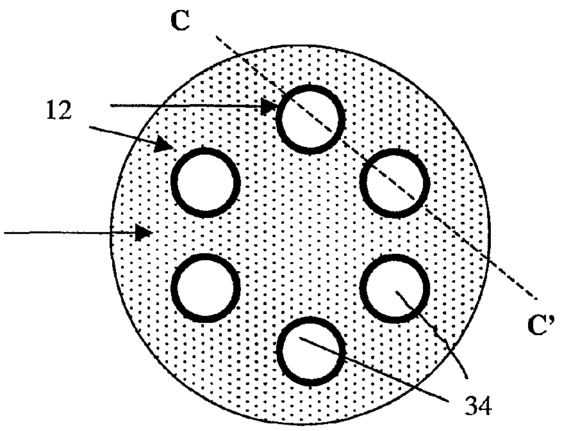
FIG. 3B is a cross sectional view along line B-B' showing an unimpeded portion of the flow tubes of FIG. 3A for liquid flow.

The treatment vessel has an even number of flow tubes 12 whereby alternating phases of high voltage electrical energy is emitted from adjacent flow tubes 12. In particular, a first flow tube may have a Phase A conductive high voltage emitter 14, while a second flow tube of these even number of flow tubes has a different, opposite Phase B conductive high voltage emitter 15. The cross-sectional view of FIG. 1, taken along line C-C' of FIG. 2A or 3A, shows two different flow tubes 12 having different phased conductive emitters 14, 15 therein residing along line A-A'. The treatment vessel assembly 100 contains an even number of these two different phased conductive emitters 14, 15, such that, each adjacent tube 12 residing along a clockwise, or counter-clockwise, path within the assembly contains an oppositely phased conductive emitter so that no two like conductive phases are adjacent or contiguous to one another. Rather, each Phase A emitter resides between two Phase B conductive emitters, while each Phase B emitter resides between two Phase A emitters.

In one or more embodiments, the Phase A conductive emitter may be a positive voltage, while the Phase B conductive emitter is an equivalent negatively charged voltage. While not meant to limit the invention, the conductive high voltage emitters 14, 15 residing within each flow tube may include, for instance, oppositely charged conductive electrodes, conductive sheets, conductive spiral brushes, a metal component, a screen, an infused conductive nylon, or any other type of material and/or component that is capable of receiving, retaining and emitting a charge to its surrounding environment. For instance, the conductive emitters 14, 15 may be positively and negatively charged electrodes, respectively.

Referring to FIGS. 1, 2A and 3A, in certain embodiments of the invention the electrodes 14, 15 may be spiral brushes each having several thousand metallic micro-spikes and barbs. These plurality of micro-spikes and barbs maximize the number of radiating points at the interface between such electrode surfaces and the liquid flow, thereby increasing the amount of electrode surface area to which the flowing liquid fuels and/or lubricants are exposed.

Regardless of the type of conductive emitters within each tube, the emitters may each be connected through a separate high voltage wire/cable 80 to an AC power source residing exterior to the outer insulating wall 5 (see, FIG. 2A). Alternatively, the emitters may be connected internally to each other via wiring inside the insulating fill material 10 whereby one or more high voltage wire/cable 80 connects these internally connected conductive emitters to the external AC power source (see, FIG. 3A). One or more holes may be provided in each flow tube 12 for connecting each tube to a high voltage wire/cable 80, whereby these holes are sealed with dielectric fill material.

In one or more embodiments of the invention, a single conductive emitter may reside substantially at the center of each flow tubes 12. As the liquid fuel and/or lubricant flows along flow path 30 and into flow path 34 portion residing within the insulting tubes 12, the liquid does not contact any conductive emitters within certain locations inside the tubes (see, e.g., along line B-B' of FIG. 1), but does make contact with conductive emitters at other locations inside the tubes (see, e.g., along line A-A' of FIG. 1). While not meant to limit the invention, referring to FIGS. 10-12, it should be appreciated that each flow tube 12 may contain two or more conductive emitters that may reside at equidistant spaced locations within the flow tubes 12. Each conductive emitter is preferably spaced equidistant from each other as well as equidistant from ends of the flow tubes to ensure a contiguous oscillating electric field within the system to which the liquid and contaminants are exposed.

As the liquid flow exits the middle portion 19 of the assembly 100, the liquid enters a second reservoir 18', which like that of the first reservoir 18, has substantially a trapezoidal prism shape with the largest diameter adjacent the exit portion of the flow tubes and middle portion, and its smallest diameter adjacent to and substantially equal to the diameter of the outlet port 17. The liquid exiting the flow tubes 12 of the middle portion enters this second reservoir 18' and is retained and circulated therein for an additional resonance treatment time before it exits the assembly through the outlet port 17.

In operation, power is supplied to the treatment vessel assembly 100 via an external AC power supply (not shown) for energizing the plurality of oppositely phased conductive emitters 14, 15 residing alternately within the tubes. Each conductive emitter emits energy corresponding to its respective phase inside the tube in which the emitter resides. As radio frequency electrical energy flows from the conductive emitters it travels through and out the tubes 12 to converge with oppositely charged energy flowing out adjacent tubes, and then at or within the reservoirs, all of this oppositely charged energy diverges from each other so that oppositely charge energy flows down into an oppositely charged tube 12 toward its emitter.

In particular, Phase A energy flows out its tube to converge with Phase B energy within the reservoirs 18, 18' and then diverges from the Phase B energy to flow down into a tube emitting Phase B energy. The Phase B energy behaves likewise. For instance, referring at least to FIG. 1, Phase A energy 14 flows out its tube to converge with Phase B 15 energy within the reservoirs 18, 18' and then diverges from the Phase B energy to flow down into the tube 12 emitting Phase B energy 15. In those embodiments where the first emitter 14 is positively charged and the second emitter 15 is negatively charged, these positive and negative energy fields initially travel out both ends of the tube in which it resides, out into the reservoirs 18, 18' and down into the oppositely charged tubes.

This energizing process generates strong oscillating radio frequency electric fields within all of the flow tubes 12 as well as within the enlarged reservoirs 18, 18'. By having alternating tubes of alternate phase charges, the system and/or apparatus is less susceptible to electro deposition or electro-shedding due to this alternating AC connection to the electrodes.

Biologically contaminated liquid fuel and/or lubricant flows along flow path 30 from the inlet port 16 and into the first reservoir 18. Once therein, the contaminated fuel and/or lubricant is retained and circulated within this reservoir for a predetermined resonance treatment time that allows the biological contaminants to be initially subjected to a first oscillating electric field 20. Again, depending upon the chemical characteristics and physical properties of the liquid and contaminant being filtered, as well as the size of the assembly itself, the resident treatment time that the liquid flow 30 is subjected to in this first electric field 20 will vary. Initial phase of microbe field interaction provides a realignment of the microbe body either in accordance with its dielectric properties or the charge distribution of a polar body, such as to maximize the effect of the treatment upon entering the flow tubes. Also, it should be appreciated that while the drawings show with the reservoir 18 as trapezoidal, this chamber or reservoir may have any shape suitable for treating liquid for a sufficient treatment time within the first field effect 20 of the invention.

The biologically contaminated liquid fuel and/or lubricant continues to flow from the first reservoir 18 and into the plurality of even number of flow tubes 12 each housing one or more electrodes. Again, one half of these conductive emitters 14, 15 (e.g., conductive electrodes 14, 15) are connected to the high voltage output transformer Phase A, while the other half are alternatingly connected to the high voltage output transformer Phase B. This arrangement generates the strong electric fields through the insulating flow tubes 12 that extend out both the inlet and outlet ends of such flow tubes 12 and loops around into the opposite phased tube 12 at both ends of such tubes. As the biologically contaminants and microbes enter into the tubes 12 they immediately encounter this high field strength alternating electrical field, which increases in intensity as such biologically contaminants and microbes approach the conductive emitters residing within the tubes 12.

As the biologically contaminants and microbes travel through the tubes 12, toward the conductive emitters 14, 15, such emitters apply additional concentrated electrical fields to the contaminants and microbes. For instance, referring to FIGS. 1, 2A and 3B, in those embodiments where the conductive emitters 14, 15 are the multiple small rod-like electrodes that fill a diameter of an inside portion of the flow tubes 12, these rod-like electrodes include numerous sharp points on surfaces of each rod. These sharp points create a number of sharp, tortuous contact points that the liquid flow, along with the biologically contaminants and microbes, must travel through.

The hundreds of rod-like electrodes and their sharp contact points have gaps of a few hundred microns to 1 mm therebetween to ensure proximal passage of all contaminants and microbes to within 1-2 microns from one or more electrodes. In doing so, these outwardly extending rods and sharp points (i.e., barbed-like rod protrusions of the electrodes) concentrate the electrical field to 20-50 times as compared to an amount obtained on a smooth surface area. As the liquid carrying the biological contaminants and microbes move away from the conductive emitters 14, 15 (e.g., conductive electrodes), such contaminants and microbes are continually exposed to electric fields as the liquid travels out the flow tube and into the second reservoir 18'. These electric fields gradually decrease as they move away from the conductive emitters residing inside the flow tubes.

As the biological contaminants and microbes move through the extensive path of oscillating radio frequency electric fields in accordance with the invention, these electric fields interfere with, alter and/or destroy the genetic make-up of these undesired biological contaminants and/or microbes within the liquid. This alteration and/or destruction of their genetic make-up has deleterious and detrimental effects on the biological contaminants and microbes, and in particular, interferes with the cell charges thereof. By disrupting their cell body charges, the invention lyses the biological contaminants and/or microbes, and after lysing continues to subject the lysed biological contaminants and/or microbes to extensive oscillating electric fields which destroys/kills the cell or causes genetic alterations that inhibit reproduction of such cell along with its eventual death. As such, the ability of these biological contaminants and microbes to form biofilms and masses within such liquid is essentially eliminated in accordance with the various embodiments of the invention, and all without generating hazardous waste for removal and disposal.

Figure 4:
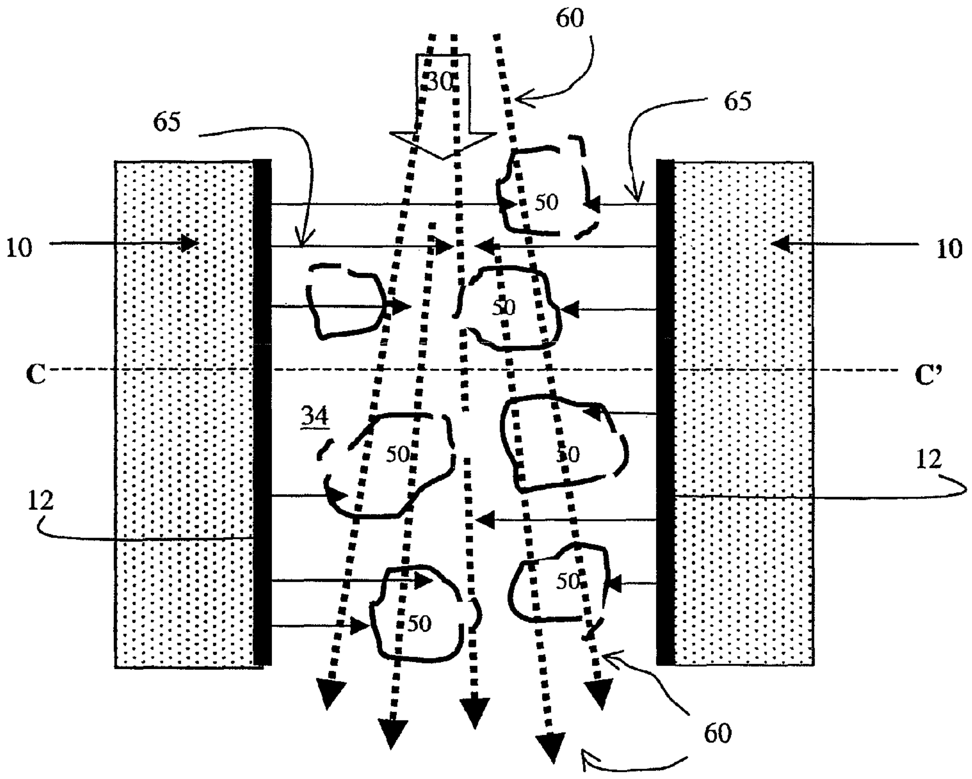
FIG. 4 is a cross sectional view of one or more embodiments of the invention showing liquid fuel flowing through one of the plurality of the flow tubes, whereby biological contaminants within the liquid flow are subjected to convergent or divergent electric fields for the deterioration and destruction thereof.
Figure 5A:
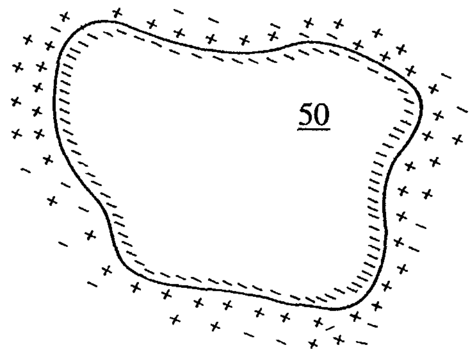
FIGS. 5A-5C illustrate an example of a biological contaminant comprising a bacteria cell that may be destroyed and/or rendered unviable in accordance with the various embodiments of the invention not limited to lysing
Figure 5B:
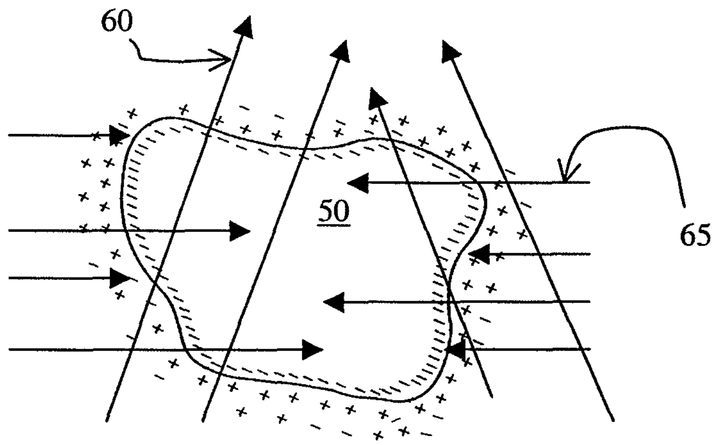
Figure 5C:
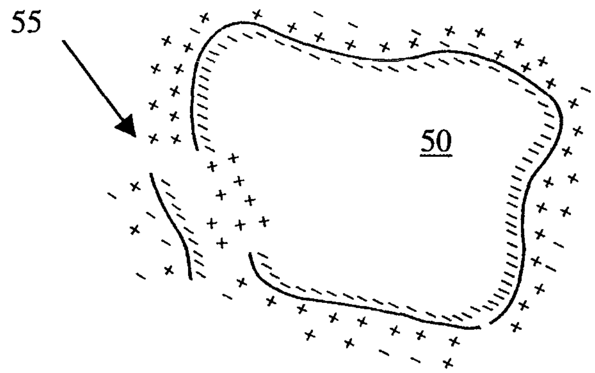

The invention may be used to eliminating and/or inhibiting contaminant cells within liquid fuels and/or lubricants may that have well defined physical structures, such as those shown in FIGS. 4-5C. In these drawings a biological contaminant or microbe 50 is shown having a defined physical structure with the perimeter (i.e., cell wall) thereof being ionically charged (e.g., negatively charged). The contaminant cell has a number of unbalanced ionic charges inside and outside of the cell, which causes the cell to be highly susceptible to electric field influence.

Again, the various embodiments of the invention generate the maximum electrical field within the insulating flow tubes at the electrodes, with continued influence in the space at the ends of the flow tubes where the fields return to tubes of opposing electrical phase. As these cells flow through the treatment vessel assembly 100, lines of the electric fields sweep 60 across the body of the cell creating mechanical forces 65 normal to the plane of the sweep 60 as shown in FIG. 5B.

Referring to FIG. 5, the influence on the treatment vessel cell is multiphase creating chemical imbalances through direct influence on ionic charges, and mechanical influence of several components, which all together have a long-term influence on morbidity and the ability of the cell to reproduce. These dielectric forces impinged upon the cells in accordance with the invention elongate the cell as a result of the electric field, and cause mechanical resonances at any site having an ionic charge. The different polar and ionic charges within the cell wall, its cytoplasm, and the cell's nucleus cause deleterious effects at each of these locations, which ultimately lead to lysing 55 of the cell, as shown in FIG. 5C. In one or more embodiments, the level of direct voltage for lysing the contaminant cell may be:

2 V=[V=1.5aE Cos θ] where:

V: is the required Voltage a: is the diameter of the cell

E: is the Electric Field

θ: is the angle between the normal to the cell wall and the electric field line.

For instance, wherein microbes being treated have diameters of about 10 microns the diameter of the cell may be about $a=10^{-5}$M and $E=1.33\times10^{5}$ v/M for the required electric field for lysing such cell. In one or more embodiments the distance between the poles may be about 25cm with a 33 KV signal to generate the required field strength for lysing unwanted cells within the treated fuel. The applied voltage may be below this threshold, and may only exceed such threshold where the geometry of the conductive emitters 14, 15 generates a field concentration due to sharp points residing on the surfaces of such emitters. In one or more embodiments, fuels suitable for use in accordance with the invention may have a boiling point of 200-300 degrees Celsius. Lubricants may have a higher boiling point. Also, voltages suitable for use in various embodiments of the invention may range from about 20 KV to about 30 KV. In certain embodiments, the systems may be equipped with a safety in the control system to disable any overly-high high voltages.

While the affects of the electric field of the invention lyses the contaminant cell, the continued exposure to the oscillating electric field of the invention, both before lysing, during lysing and after lysing, alters the genetic make-up of such cells to destroy and/or eliminate each cells ability to reproduce. This prevents biofilm and biomass formation within the liquid fuels and/or lubricants being treated. Also, electrolysis of aqueous matter within the cell body may occur at high electric potentials. In the invention, the convergent field lines at the inlet ends of each flow tube each have an orienting effect on the biological contaminants and microbes under dielectric forces.

Since the numerous embodiments of the invention destroy and/or deleteriously affect the reproductive capabilities of biological contaminants and/or microbes within the treated effluent, the contaminant cells are not able to grow and reproduce such that biofilm and biomass growth does not occur. That is, the invention prohibits and prevents the growth of biofilms and biomasses within liquid fuels and/or lubricants due to the residuum effect from the electrical activity within the flow tubes.

The various embodiments of the invention affect the contaminant cells in a number of ways. Some of the ways in which the cells are affected include, but are not limited to, disrupting the ionic structure of the cell, damaging the proteins which regulate Ph, disrupting the genome which makes up the cell nucleus, damaging/destroying the nucleotides in the cytoplasm that are essential for mitosis or meiosis, causing electrolysis within the cell (>20 Volts measured across the cell), or disrupting the chemical balance within the cell trough electroporation. Any combination of the foregoing is also possible in accordance with the invention.

Figure 10:
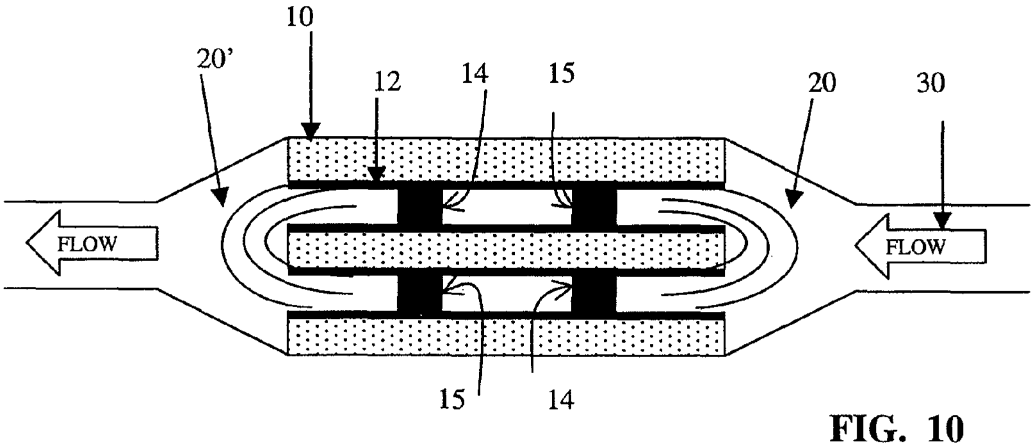
FIGS. 10-12 show cross sectional side views of alternate treatment vessel assemblies in accordance with the various embodiments of the present invention.
Figure 11:
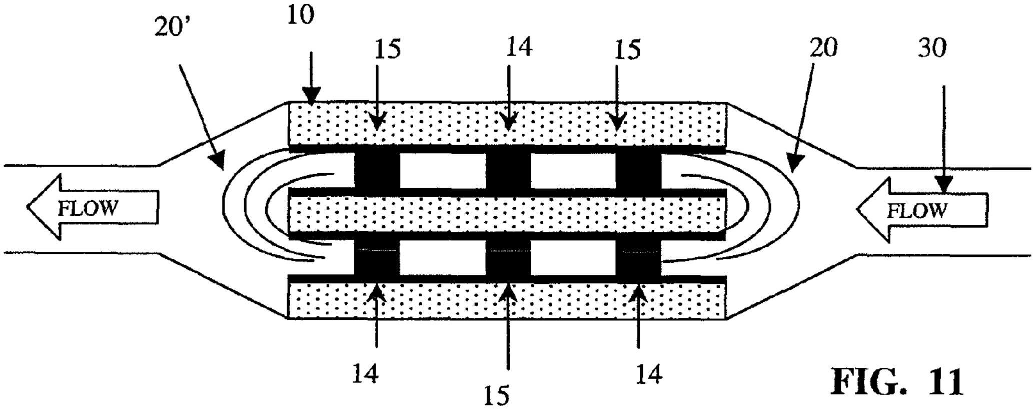
Figure 12:
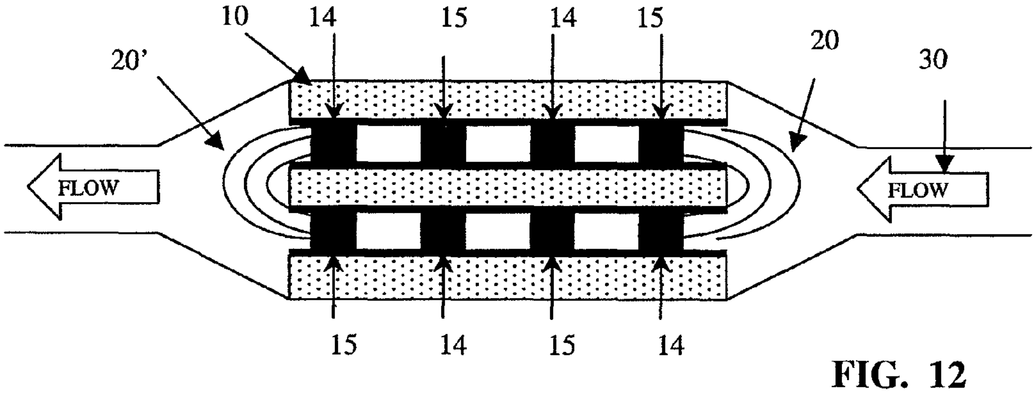

It is again to be appreciated and understood that the present invention is not limited to a single conductive emitter residing substantially at the center of each flow tube 12. Referring to FIGS. 10-12 multiple conductive emitters (e.g., multiple conductive electrodes) may reside at various locations within each flow tube 12. Multiple electrodes may provide reduced pole-to-pole voltages for bacteria where multiple lower voltages and multiple saturations may be more effective for such bacteria as compared to a same electric field with a single saturation.

FIGS. 6-9 depict tables of experimental results and graphical representation thereof. In experimentation, an amount of a liquid fuel having biological contaminants and/or microbes was treated in a single pass through a treatment vessel assembly of the invention, thereby treating the biological contaminants and/or microbes within such liquid to the extensive oscillating electric fields of the invention. The effluent was provided into a beaker containing water in the bottom portion thereof so that the treated fuel of the invention resided over the water. A standard microscope slide, rigorously cleaned, rested at an angle from near the center of the beaker to roughly the 80% point on the side of the beaker to allow any bacteria in the fuel to migrate by surface tension to the boundaries of the beaker or slide, or remain at the oil/water interface as a replication site.

Figures 6, 7:
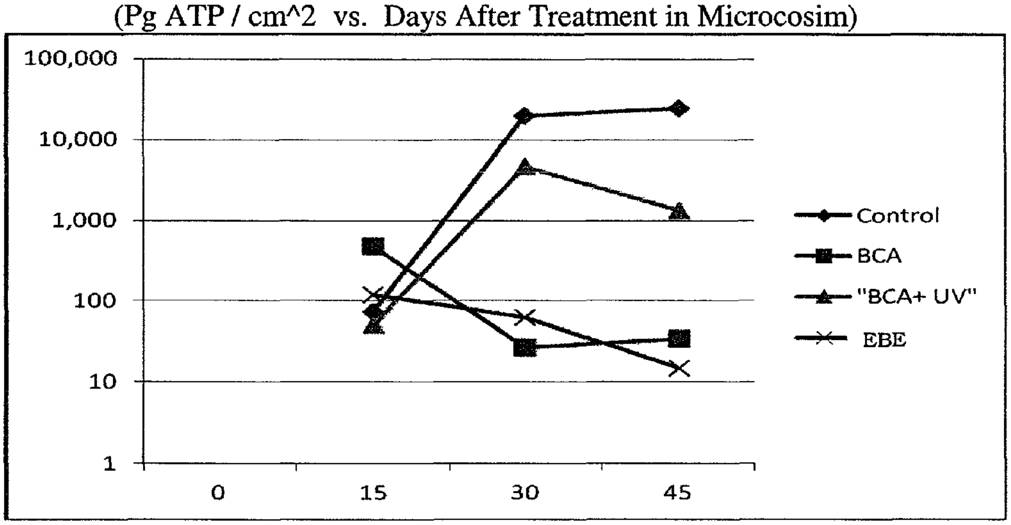
FIG. 6 is a table showing results of the invention in comparison to other non-chemical biological contaminant elimination treatment approaches, all cultured in the fuel phase.
FIG. 7 is a graph representation of the results and data shown in the Table of FIG. 6.

The treated fuel was allowed to culture in this static microcosm for a number of different days as set forth in the table of FIG. 6, and the results thereof analyzed at set day intervals. To compare the results of the invention, experimentation of the same liquid fuel were performed using known filtering approaches, namely, a control (i.e., no treatment done), treatment by non-specific electrical treatment a balanced charge agglomeration (BCA), and treatment by BCA in combination with ultraviolet (UV) treatment. The results in accordance with the invention are indicated as "EBE" within the table of FIG. 6. The glass microscope slides from the various samples were removed, and the glass slides side that was within the fuel phase was observed for measuring the ATP per $cm^2$ biomass in the fuel phase at the days indicated (i.e., presence of contaminant cell count measured in the fuel phase).

As is shown, all test samples began to replicate and collect on the glass coupon during the first two-week period as measured at day 15. As the days progressed the ATP biomass count of the control and BCA+UV runs dramatically increased, while the BCA and inventive EBE run had a decrease in ATP biomass count (however, it should be noted that the BCA run generates toxic waste that must be disposed of). These experimental results were plotted in the graph depicted in FIG. 7.

The successful results of the invention (the EBE results) show that all of the aggregate biomass on the slide associated with the EBE run suffered irreversible damage and was unable to continue reproduction. This was not found with all of the other know approaches tested. As expected, the control (non-treatment) run experienced the most biofilm development (between $10^4$ and $10^7$ pg ATP/cm$^2$). The results of the invention establish that the invention demonstrates a negative growth rate after day 15 due to exposure of the contaminants to the electric fields in the full length of the flow tubes and in the return fields at either end of such flow tubes. After day 15, the growth trended in a negative direction with no regrowth thereafter.

Figures 8, 9:
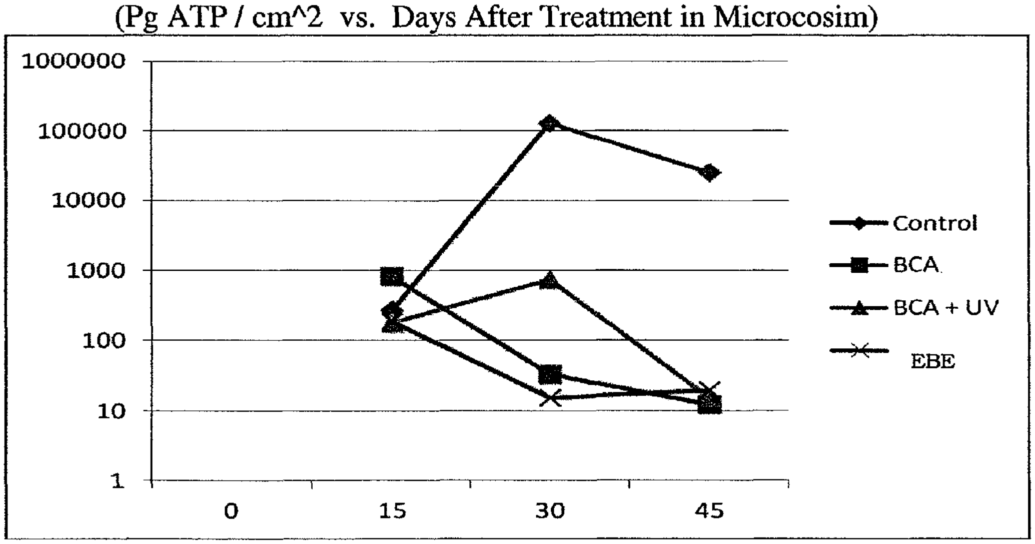
FIG. 8 is a table showing additional results of the invention in comparison to other known biological contaminant elimination treatment approaches, all cultured in the water phase following fuel only treatment.
FIG. 9 is a graph representation of the results and data shown in the Table of FIG. 8.

These results of the invention were verified by also measuring ATP per cm$^2$ biomass in the water (originally sterile) phase from such samples, and the results of the invention compared against the known techniques. The table of FIG. 8 shows the ATP biomass on the glass slides side that were incubating in the water phase for measuring the ATP per cm$^2$ biomass in such water phase at the days indicated, while FIG. 9 shows the plotted graphical depiction of such results. As observed, the results confirmed the negative growth of any remaining biological contaminants and/or microbes present within the fuel treated in accordance with the invention.

While the present invention has been particularly described, in conjunction with one or more preferred embodiments, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

Thus, having described the invention, what is claimed is:

1. A treatment apparatus for inhibiting biological contaminant proliferation within fuels and lubricants comprising:

exterior walls defining a cavity of the treatment apparatus;

an insulating fill material within a portion of the cavity;

an even number of a plurality of insulating flow tubes encased within the insulating fill material, the insulating fill material isolating the flow tubes from one another;

at least one reservoir residing in fluid communication with the plurality of insulating flow tubes within the cavity; and at least one conductive body within each of the plurality of insulating flow tubes, adjacent ones of the plurality of insulating flow tubes having alternating oppositely charged conductive phases of energy to generate an oscillating electric field within the plurality of insulating flow tubes and within the at least one reservoir to treat biological contaminants within fluid fuels and/or lubricants flowing through the treatment apparatus, wherein the at least one conductive body within each of the plurality of insulating flow tubes comprise oppositely charged electrodes, a first set of the plurality of insulating flow tubes containing positively charged electrodes and a second set of the plurality of insulating flow tubes containing negatively charged electrodes, the positively charged electrodes and negatively charged electrodes residing in alternating flow tubes so that positively charged electrodes are not contiguous with other positively charged electrodes while negatively charged electrodes are not contiguous with other negatively charged electrodes.

2. The apparatus of claim 1 wherein the exterior walls of the treatment apparatus comprise an insulating material.

3. The apparatus of claim 2 wherein the insulating material is selected from the group consisting of plastic, PVC, glass, fiberglass and nylon.

4. The apparatus of claim 1 wherein the insulating fill material comprises a material selected from the group consisting of an epoxy, silicon, a plastic, and a dielectric material.

5. The apparatus of claim 1 wherein the plurality of flow tubes comprise a material having a dissipation factor that prevents over-heating and a low dielectric constant that prevents influencing the oscillating electric field.

6. The apparatus of claim 5 wherein the plurality of flow tubes comprise an insulating material selected from the group consisting of plastic, PVC, fiberglass, nylon, glass and a fluorocarbon polymer.

7. The apparatus of claim 1 wherein the treatment apparatus further includes an fluid flow inlet port on one side of the plurality of insulating flow tubes and a fluid flow outlet port an opposite side of the flow tubes.

8. The apparatus of claim 1 wherein the treatment apparatus comprises a first reservoir at a fluid inlet side of the plurality of insulating flow tubes and a second reservoir at a fluid outlet side of the plurality of insulating flow tubes, the oscillating electric field residing within the first reservoir, the plurality of insulating flow tubes and the second reservoir, and the first and second reservoirs each having a shape that allows a fluid flow to circulate within said reservoirs for a predetermined treatment time to treat the fluid flow with the oscillating electric field at the first and second reservoirs and at the plurality of insulating flow tubes.

9. The apparatus of claim 8 wherein the insulating fill material encasing the plurality of insulating flow tubes each having the at least one conductive body residing at a middle portion of the treatment apparatus, and the first reservoir resides between an inlet port and the middle portion of the treatment apparatus while the second reservoir resides between the middle portion of the treatment apparatus and an outlet port.

10. The apparatus of claim 1 wherein the at least one conductive body in each of the plurality of insulating flow tubes are selected from the group consisting of conductive electrodes, conductive sheets, a screen, conductive spiral brushes, conductive metals and an infused conductive nylon.

11. The apparatus of claim 1 wherein the at least one conductive body within each of the plurality of insulating flow tubes comprise spiral brushes each having micro-spikes and barbs.

12. The apparatus of claim 1 wherein a single conductive body resides substantially at the middle of each of the plurality of insulating flow tubes.

13. The apparatus of claim 1 wherein two or more conductive bodies reside in each of the plurality of insulating flow tubes, the two or more conductive bodies residing equidistant from each other and equidistant from ends of their respective insulating flow tubes.

14. The apparatus of claim 13 wherein the two or more conductive bodies within each of the plurality of insulating flow tubes emit alternating opposing phases of charged energy.

15. A treatment system for inhibiting biological contaminant proliferation within fuels and lubricants comprising:

a treatment apparatus with a defined cavity having an insulating fill material encasing a number of insulating flow tubes each having at least one conductive body therein, the defined cavity also having at least one reservoir in communication with the insulating flow tubes, the at least one conductive body within each of the plurality of insulating flow tubes comprise oppositely charged electrodes, a first set of the plurality of insulating flow tubes containing positively charged electrodes and a second set of the plurality of insulating flow tubes containing negatively charged electrodes, the positively charged electrodes and negatively charged electrodes residing in alternating flow tubes so that positively charged electrodes are not contiguous with other positively charged electrodes while negatively charged electrodes are not contiguous with other negatively charged electrodes;

a radio frequency oscillating electric field within the insulating flow tubes and within the at least one reservoir, the radio frequency oscillating electric field generated by the conductive bodies within the insulating flow tubes; and a biological contaminated fluid flowing through the treatment apparatus and contacting the radio frequency oscillating electric field within the insulating flow tubes and within the at least one reservoir, the radio frequency oscillating electric field affecting the biological contaminants within the fluid to inhibit the proliferation thereof within said fluid.

16. The system of claim 15 wherein the biological contaminated fluid is selected from the group consisting of a biological contaminated liquid fuel, a biological contaminated liquid lubricant, and a biological contaminated liquid fuel and lubricant mixture.

17. The system of claim 15 further including the insulating fill material encasing the number of insulating flow tubes residing between first and second reservoirs and each having the oscillating electric field, whereby the fluid flows through the first reservoir having the oscillating electric field for a first treatment time, through the flow tubes having the oscillating electric field for a second treatment time, and through the second reservoir having the oscillating electric field for a third treatment time.

18. The system of claim 15 wherein each insulating flow tube has two or more conductive bodies residing therein each emitting alternating opposing phases of charged energy for generating the oscillating electric field within the treatment system.

* * * * *